United States Patent
Choi et al.

(10) Patent No.: US 12,292,439 B2
(45) Date of Patent: May 6, 2025

(54) METHOD FOR MANUFACTURING SURFACE-ENHANCED RAMAN SCATTERING-BASED SUBSTRATE FOR DETECTING TARGET SUBSTANCE, SUBSTRATE MANUFACTURED THEREBY FOR DETECTING TARGET SUBSTANCE, AND METHOD FOR DETECTING TARGET SUBSTANCE BY USING SAME SUBSTRATE

(71) Applicant: Exopert Corporation, Seoul (KR)

(72) Inventors: Yeon Ho Choi, Seoul (KR); Hyun Ku Shin, Seoul (KR)

(73) Assignee: Exopert Corporation, Seoul (KR)

( * ) Notice: Subject to any disclaimer, the term of this patent is extended or adjusted under 35 U.S.C. 154(b) by 984 days.

(21) Appl. No.: 17/311,720

(22) PCT Filed: Mar. 27, 2020

(86) PCT No.: PCT/KR2020/004161
§ 371 (c)(1),
(2) Date: Jun. 8, 2021

(87) PCT Pub. No.: WO2020/197305
PCT Pub. Date: Oct. 1, 2020

(65) Prior Publication Data
US 2022/0026423 A1  Jan. 27, 2022

(30) Foreign Application Priority Data

Mar. 27, 2019  (KR) .................. 10-2019-0035295

(51) Int. Cl.
| | |
|---|---|
| *G01N 1/38* | (2006.01) |
| *B82Y 5/00* | (2011.01) |
| *B82Y 40/00* | (2011.01) |
| *G01N 21/65* | (2006.01) |
| *G01N 33/543* | (2006.01) |
| *G01N 33/553* | (2006.01) |

(52) U.S. Cl.
CPC ......... *G01N 33/54346* (2013.01); *G01N 1/38* (2013.01); *G01N 21/658* (2013.01); *G01N 33/553* (2013.01); *B82Y 5/00* (2013.01); *B82Y 40/00* (2013.01); *G01N 2001/386* (2013.01)

(58) Field of Classification Search
CPC .......... G01N 33/54346; G01N 21/658; G01N 33/54373
USPC ......................................................... 436/525
See application file for complete search history.

(56) References Cited

U.S. PATENT DOCUMENTS

| | | | | |
|---|---|---|---|---|
| 6,149,868 A | * | 11/2000 | Natan | G01N 21/658 436/164 |
| 2012/0202225 A1 | * | 8/2012 | Knutson | G01N 33/80 435/7.25 |

FOREIGN PATENT DOCUMENTS

| | | | | |
|---|---|---|---|---|
| JP | 2005233637 A | * | 9/2005 | .......... G01N 21/658 |
| KR | 10-2009-0083685 A | | 8/2009 | |
| KR | 10-2013-0085579 A | | 7/2013 | |
| KR | 10-2014-0127463 A | | 11/2014 | |
| KR | 10-2016-0021488 A | | 2/2016 | |
| KR | 20160021488 A | * | 2/2016 | |
| KR | 10-1691067 B1 | | 12/2016 | |

OTHER PUBLICATIONS

Yang et al., Ultra-sensitive immunoassay biosensors using hybrid plasmonic-biosilica nanostructured materials, J. Biophotonics 8, No. 8, 659-667 (2015). (Year: 2015).*
Lim et al., Gold and magnetic oxide/gold core/shell nanoparticles as bio-functional nanoprobes, Nanotechnology 19 (2008) 305102 (11pp). (Year: 2008).*
International Search Report issued on Jul. 9, 2020 in counterpart International Patent Application No. PCT/KR2020/004161 (2 pages in English and 2 pages in Korean).
Yang, Jing, et al. "Ultra-sensitive immunoassay biosensors using hybrid plasmonic-biosilica nanostructured materials." Journal of biophotonics 8.8 (2015): 659-667.
Wang, Zhuyuan, et al. "SERS-Activated Platforms for Immunoassay: Probes, Encoding Methods, and Applications." Chemical reviews 117.12 (2017): 7910-7963.

* cited by examiner

*Primary Examiner* — Gregory S Emch
*Assistant Examiner* — Omar Ramadan
(74) *Attorney, Agent, or Firm* — NSIP Law

(57) ABSTRACT

The present disclosure relates to a method for manufacturing a surface-enhanced Raman scattering (SERS)-based substrate for detecting a target substance, by which the surface of a target substance can be easily coated with metal nanoparticles through centrifugation, a substrate for detecting a target substance manufactured thereby, and a method for detecting a target substance using the same.

10 Claims, 8 Drawing Sheets

METHOD FOR MANUFACTURING SURFACE-ENHANCED RAMAN SCATTERING-BASED SUBSTRATE FOR DETECTING TARGET SUBSTANCE, SUBSTRATE MANUFACTURED THEREBY FOR DETECTING TARGET SUBSTANCE, AND METHOD FOR DETECTING TARGET SUBSTANCE BY USING SAME SUBSTRATE

CROSS REFERENCE TO RELATED APPLICATIONS

This application is a U.S. National Stage Application of International Application No. PCT/KR2020/004161, filed on Mar. 27, 2020, which claims the benefit under 35 USC 119(a) and 365(b) of Korean Patent Application No. 10-2019-0035295, filed on Mar. 27, 2019, in the Korean Intellectual Property Office, the entire disclosure of which is incorporated herein by reference for all purposes.

TECHNICAL FIELD

The present disclosure relates to a method for manufacturing a surface-enhanced Raman scattering (SERS)-based substrate for detecting a target substance, a substrate for detecting a target substance manufactured thereby, and a method for detecting a target substance using the same.

BACKGROUND ART

Surface-enhanced Raman scattering (SERS) is one of the most promising analysis methods. It is a spectroscopic method of, when an analyte is adsorbed on the surface of a Raman-active material such as a roughened metal or is located within a distance of hundreds of nanometers, measuring the Raman scattering intensity of the analyte, which has been increased by 104-106 times or more due to surface plasmons provided by the surface roughness.

Because the wavelength of a Raman emission spectrum informs the chemical composition and structural characteristics of light-absorbing molecules in the sample, the analyte may be analyzed directly by analyzing the Raman signal.

In protein analysis, the existing methods of detecting the intrinsic SERS signals of proteins have been focused on single proteins in a sample or isolated and purified proteins. However, in an actual biological sample, various complex substances exist together and a large amount of sample is required for separating/purifying the target protein prior to detection. A simple method of separating/purifying the target protein in advance is to utilize immunological binding using antibodies, etc. For example, composite particles prepared by binding an antibody specific to a target protein on the surface of metal particles and then binding the target protein to the antibody have been used.

Meanwhile, the intensity of the SERS signal decreases exponentially depending on the distance from the nanogap. Since the composite particles described above have a predetermined distance between the surface of the metal particles and the target protein, detection sensitivity is low.

In addition, they have not been commercialized because time-consuming and cost-intensive high-performance equipment such as focused ion-beam lithography, e-beam lithography, ion milling, etc. is necessary for manufacturing of a nanostructure exhibiting strong sensitivity.

Accordingly, a convenient process for manufacturing of a sensor requiring no additional separation/purification of proteins is necessary, and a biosensor, etc. capable of uniform signal detection is necessary.

DISCLOSURE

Technical Problem

The present disclosure is directed to providing a convenient method for manufacturing a surface-enhanced Raman scattering (SERS)-based substrate for detecting a target substance, a substrate for detecting a target substance manufactured thereby, and a method for detecting a target substance using the same.

Technical Solution

The present disclosure provides a method for manufacturing a surface-enhanced Raman scattering (SERS)-based substrate for detecting a target substance, which includes:
a step of forming a primary capture structure with a target substance and a bioreceptor bound by immersing a bioreceptor-attached substrate in a sample solution containing a target substance;
a step of disposing the substrate with the primary capture structure formed in a centrifuge and adding a solution containing metal nanoparticles into the centrifuge; and
a step of forming a secondary capture structure coating the metal nanoparticles on the surface of the target substance by operating the centrifuge.

In addition, the present disclosure provides a surface-enhanced Raman scattering (SERS)-based substrate for detecting a target substance, which includes:
a bioreceptor-attached substrate;
a target substance captured by the bioreceptor;
metal nanoparticles capping the target substance; and
a Raman dye attached to the metal nanoparticles,
wherein the target substance is sandwiched between the bioreceptor and the metal nanoparticles to form a capture structure.

In addition, the present disclosure provides a surface-enhanced Raman scattering (SERS)-based method for detecting a target substance, which detects a target substance using a surface-enhanced Raman scattering (SERS)-based substrate for detecting a target substance.

Advantageous Effects

According to a method for manufacturing a surface-enhanced Raman scattering (SERS)-based substrate for detecting a target substance of the present disclosure, metal nanoparticles may be coated quickly and uniformly on the surface of a target substance through centrifugation.

In addition, by coating the metal nanoparticles directly on the target substance, the distance between the surface of the metal particles and the target substance may be reduced and, accordingly, the detection sensitivity of the target substance may be increased and the target substance may be detected easily based on surface-enhanced Raman scattering (SERS).

BRIEF DESCRIPTION OF DRAWINGS

FIG. 8A shows a result of analyzing spectra while moving detection spots with 2-μm intervals up to 120 μm, and FIG. 8B shows a result of analyzing spectra for randomly chosen detection spots.

BEST MODE

The present disclosure may be changed variously and may have various exemplary embodiments. Hereinafter, specific exemplary embodiments will be described in detail referring to the attached drawings.

However, it is not intended to limit the present disclosure to the specific exemplary embodiments, and it should be understood that all changes, equivalents and substitutes included in the technical spirit and scope the present disclosure are included. When describing the present disclosure, detailed description of known technology will be omitted to avoid obscuring the subject matter of the present disclosure.

The terms used in the present disclosure are used merely for illustration of specific exemplary embodiments and are not intended to limit the present disclosure. Singular forms include plural referents unless the context clearly indicates otherwise.

In the present disclosure, the terms such as "includes" or "has" are intended to indicate the existence of characteristics, figures, steps, operations, constituents, components or combinations thereof disclosed in the present disclosure, and should be understood as not precluding the possibility of existence or addition of one or more other characteristics, figures, steps, operations, constituents, components or combinations thereof.

The present disclosure relates to a method for manufacturing a surface-enhanced Raman scattering (SERS)-based substrate for detecting a target substance, a substrate for detecting a target substance manufactured thereby, and a method for detecting a target substance using the same. More specifically, it relates to a method for manufacturing a surface-enhanced Raman scattering (SERS)-based substrate for detecting a target substance by coating metal nanoparticles on an immunologically attached target substance using a centrifugation process, a substrate for detecting a target substance manufactured thereby, and a method for detecting a target substance using the same.

In particular, according to the method for manufacturing a surface-enhanced Raman scattering (SERS)-based substrate for detecting a target substance of the present disclosure, metal nanoparticles may be coated quickly and uniformly on the surface of a target substance through centrifugation.

In addition, by coating the metal nanoparticles directly on the target substance, the distance between the surface of the metal particles and the target substance may be reduced and, accordingly, the detection sensitivity of the target substance may be increased and the target substance may be detected easily based on surface-enhanced Raman scattering (SERS).

Figure 1:
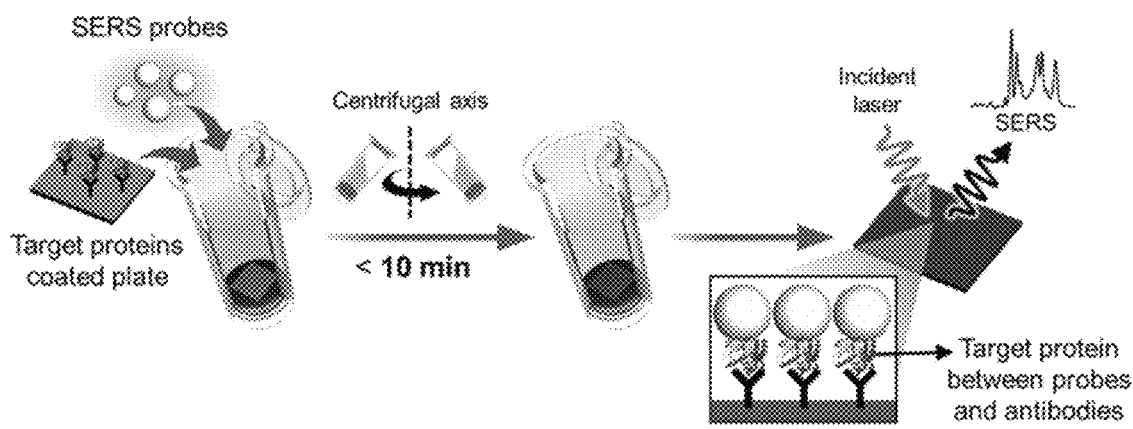
FIG. 1 schematically shows a process of manufacturing a surface-enhanced Raman scattering (SERS)-based substrate for detecting a target substance according to an exemplary embodiment of the present disclosure.

Hereinafter, the present disclosure is described in detail. FIG. 1 schematically shows a process of manufacturing a surface-enhanced Raman scattering (SERS)-based substrate for detecting a target substance according to an exemplary embodiment of the present disclosure, and FIG. 2 is a flow chart showing a process of manufacturing a surface-enhanced Raman scattering (SERS)-based substrate for detecting a target substance according to an exemplary embodiment of the present disclosure.

Figure 2:
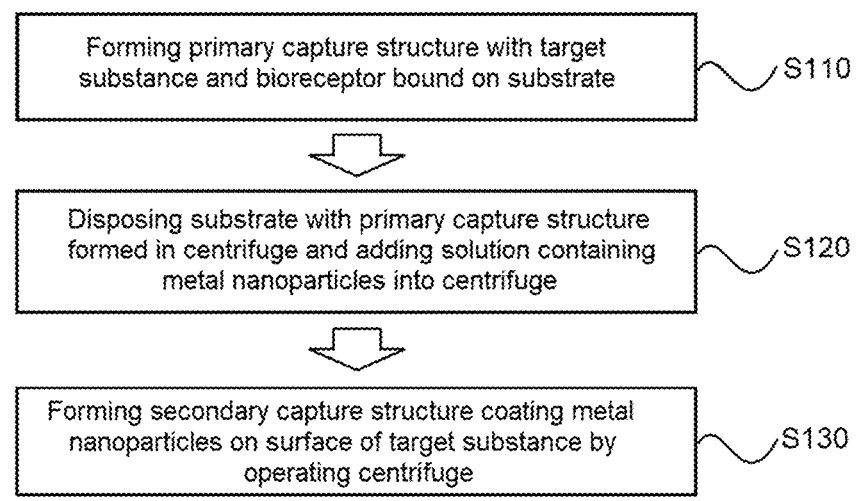
FIG. 2 is a flow chart showing a process of manufacturing a surface-enhanced Raman scattering (SERS)-based substrate for detecting a target substance according to an exemplary embodiment of the present disclosure.

Referring to FIG. 1 and FIG. 2, the method for manufacturing a surface-enhanced Raman scattering (SERS)-based substrate for detecting a target substance according to the present disclosure includes:

a step of forming a primary capture structure with a target substance and a bioreceptor bound by immersing a bioreceptor-attached substrate in a sample solution containing a target substance (S110);

a step of disposing the substrate with the primary capture structure formed in a centrifuge and adding a solution containing metal nanoparticles into the centrifuge (S120); and a step of forming a secondary capture structure coating the metal nanoparticles on the surface of the target substance by operating the centrifuge (S130).

The term "bioreceptor-attached substrate" used in in the present disclosure may refer to a substrate on which a bioreceptor is immobilized by surface treatment of the substrate.

The bioreceptor-attached substrate may be one prepared by a step of attaching a bioreceptor to a substrate by immersing the substrate in a solution containing a surface modifier and a bioreceptor; and a step of attaching a blocking molecule onto a portion of the surface of the substrate without the bioreceptor attached.

The surface modifier is used for easy attachment of a bioreceptor to the substrate and may be one or more selected from a group consisting of (3-aminopropyl)triethoxysilane (APTES), (3-aminopropyl)trimethoxysilane (APTMS), cysteamine, N-[3-(trimethoxysilyl)propyl]ethylenediamine (AEAPTMS), (3-mercaptopropyl)trimethoxysilane (MPTMS), (3-mercaptopropyl)triethoxysilane (MPTES), mercaptopropionic acid (MPA), 6-mercaptohexanoic acid (MHA), 1,4-benzenedithiol (BDT), 4-mercaptobenzoic acid (MBA) and 2-mercaptobenzoimidazole-5-carboxylic acid (MBIA), although not being necessarily limited thereto. In a specific exemplary embodiment, it may be APTES.

For example, a substrate modified with an amine group ($-NH_2$) may be prepared. As another exemplary embodiment, a thiol group ($-SH$) may be used as an anchoring group for immobilizing a bioreceptor through further treatment.

The "bioreceptor" refers to a substance which is specific for a target substance and is capable of capturing the target substance by being immobilized on a substrate, and may include a substance which has binding affinity for the target substance. For example, the bioreceptor may be an "antibody", and the antibody refers to a protein consisting of amino acids and sugar chains, which can bind to the target substance.

Although the bioreceptor is not limited in type, it may be selected from a group consisting of a protein antibody, an aptamer, an enzyme, a nucleic acid, a DNA, an RNA, a cell, a biometic, protein, an organic compound and a polymer in a specific exemplary embodiment. An adequate bioreceptor may be selected depending on the type of the target substance. For example, when the target substance is cyt c, the bioreceptor may be a protein antibody.

In a specific exemplary embodiment, a bioreceptor-attached substrate may be prepared by immersing a substrate in a solution containing a substance for surface modification of the substrate and a bioreceptor.

The substrate may be a nonmetallic material selected from a group consisting of silicon (Si), gallium arsenide (GaAs), glass, quartz and a polymer, although not being necessarily limited thereto. In a specific exemplary embodiment, the substrate may be glass.

Meanwhile, blocking molecules may be attached to a substrate with no bioreceptor attached. The blocking molecule may be one or more selected from a group consisting of bovine serum albumin (BSA), casein and skim milk. As a specific exemplary embodiment, the blocking molecule may be bovine serum albumin (BSA).

The blocking molecules may serve to maintain the orientation of the bioreceptor constant by being attached on the surface of the substrate. As a result, binding with a target substance may be facilitated as the binding site of the bioreceptor is easily exposed.

In addition, the blocking molecules may be bound to the remaining sites of the substrate on which the bioreceptor is not located and, thus, may prevent the metal nanoparticles form binding directly to the substrate or the bioreceptor.

Then, in order to perform centrifugal coating according to the present disclosure, the substrate or a substrate with the primary capture structure formed is disposed in a centrifuge. Here, the centrifuge in which the substrate is mounted may refer to a centrifuge tube. Specifically, the substrate may be disposed to be spaced apart from the bottom of the centrifuge. More specifically, in order to make the bottom surface of the centrifuge tube flat, a support made of a material such as PDMS, etc. may be placed on the bottom surface of the tube and then the substrate may be placed thereon.

Moreover, in order to coat metal nanoparticles on the surface of the protein of the primary capture structure, a solution containing metal nanoparticles may be added into the centrifuge (or centrifuge tube).

The metal nanoparticles contained in the solution may be one or more selected from a group consisting of gold (Au), silver (Ag), platinum (Pt) and aluminum (Al), although not being necessarily limited thereto. In a specific exemplary embodiment, the metal nanoparticles may be gold (Au) nanoparticles. The substrate according to the present disclosure exhibits superior signal amplification ability and signal uniformity when the metal nanoparticles are prepared from the above-described metals.

The metal nanoparticles may have a diameter of 10-100 nm on average. The metal nanoparticles may have a diameter of 20-95 nm, 40-90 nm, 60-95 nm or 80 nm on average. For example, when the diameter of the metal nanoparticles is smaller than 10 nm, it may be impossible to settle down the nanoparticles through centrifugation. And, when the diameter of the metal nanoparticles exceeds 100 nm, synthesis may be impossible.

The solution containing the metal nanoparticles may have a concentration of $1\times10^9$ to $1\times10^{12}$ particles/mL on average. When the concentration of the solution containing the metal nanoparticles is below $1\times10^9$ particles/mL, a sufficient amount of the nanoparticles may not be coated on the surface of the target substance. And, when the concentration exceeds $1\times10^{12}$ particles/mL, the nanoparticles may be accumulated excessively on the surface of the target substance. In other words, when coating the metal nanoparticles on the surface of the target substance through centrifugation, the thickness of a metal layer formed on the substrate may be controlled by adjusting the concentration of the metal nanoparticle solution.

After the disposition of the substrate in the centrifuge and the addition of the metal nanoparticle solution are completed, the metal nanoparticles may be coated on the surface of the target substance by operating the centrifuge.

More specifically, in the step of forming the secondary capture structure, the centrifuge may be operated at 1,000-6,000×g for 2-5 minutes. In a specific exemplary embodiment, gold nanoparticles with an average diameter of 80 nm may be centrifuged at 1,000×g for 3 minutes.

In the step of forming the secondary capture structure through centrifugation, a capture structure may be formed as the target substance is sandwiched between the bioreceptor and the metal nanoparticles. That is to say, a "sandwich immune complex" may be formed. In the present disclosure, the "sandwich immune complex" refers to an immune complex formed through an antibody-antigen-antibody reaction. It is named so because the antigen is sandwiched between the antibodies. In the present disclosure, the sandwich immune complex may have a bioreceptor-target substance-metal nanoparticle structure. Through centrifugation, the metal nanoparticles come close to the target substance on the bottom surface of the tube and the nanoparticles may be attached to and coated on the target substance by electrostatic or hydrophobic interaction, hydrogen bonding, van der Waals force or steric hindrance between the target substance and the metal nanoparticles.

Particularly, whereas the distance between a target substance and metal nanoparticles has been mostly maintained to tens of nanometers by an antibody in the prior art, in the present disclosure, the distance between the target substance and the metal nanoparticles is smaller than 1 nm because the target substance is coated directly on the metal nanoparticles. As a result, the SERS signal can be enhanced and improved very superiorly.

The step of forming the secondary capture structure through centrifugation may be repeated 3 times or more. More specifically, the centrifugation process may be repeated 3-7 times, 3-6 times, 3-5 times or 4 times. In a specific exemplary embodiment, as the centrifugation process is repeated, the intensity of a signal may be increased during the detection of the target substance based on SERS. However, since the increase of the signal intensity is saturated after repletion of about 4 times, it is preferred that the centrifugation process is repeated 4 times in consideration of the easiness of reproducible detection and economy.

In addition, the method may further include, a step of attaching a Raman dye on the surface of the metal nanoparticles. The Raman dye refers to a Raman-active organic compound for detection by surface-enhanced Raman scattering (SERS) spectroscopy, and any one commonly used in the art may be used without limitation.

For example, the Raman dye may be selected from a group consisting of malachite green isothiocyanate (MGITC), rhodamine B isothiocyanate (RBITC), rhodamine 6G, adenine, 4-aminopyrazolo[3,4-d]pyrimidine, 2-fluoroadenine, $N^6$-benzoyladenine, kinetin, dimethylallylaminoadenine, zeatin, bromoadenine, 8-azaadenine, 8-azaguanine, 4-mercaptopyridine, 6-mercaptopurine, 4-amino-6-mercaptopyrazolo[3,4-d]pyrimidine, 8-mercaptoadenine, 9-aminoacridine and a mixture thereof, although not being necessarily limited thereto.

Figure 3:
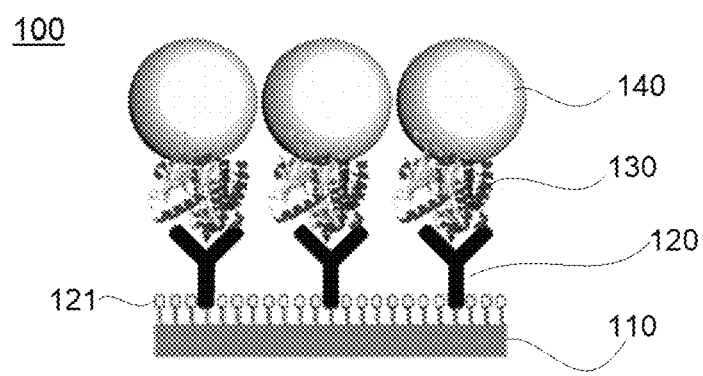
FIG. 3 schematically shows a surface-enhanced Raman scattering (SERS)-based substrate for detecting a target substance according to an exemplary embodiment of the present disclosure.

FIG. 3 schematically shows a surface-enhanced Raman scattering (SERS)-based substrate for detecting a target substance according to an exemplary embodiment of the present disclosure.

Referring to FIG. 3, the surface-enhanced Raman scattering (SERS)-based substrate for detecting a target substance 100 according to the present disclosure includes:

a substrate 110 to which a bioreceptor 120 is attached;
a target substance 130 captured by the bioreceptor 120;
metal nanoparticles 140 capping the target substance 130; and
a Raman dye (not shown) attached to the metal nanoparticles 140,
wherein the target substance 130 is sandwiched between the bioreceptor 120 and the metal nanoparticles 140 to form a capture structure.

Here, the "substrate 110 to which a bioreceptor 120 is attached" may refer to a substrate 110 on which the bioreceptor 120 is immobilized by surface treatment of the substrate 110.

The substrate 110 to which a bioreceptor 120 is attached may be a substrate 110 surface-modified by a surface modifier. For example, the bioreceptor 120 may be attached to a substrate modified by an amine group (—$NH_2$).

The "bioreceptor" refers to a substance which is specific for the target substance 130 and is capable of capturing the target substance 130 by being immobilized on the substrate 110, and may include a substance which has binding affinity for the target substance 130. For example, the bioreceptor 120 may be an "antibody", and the antibody refers to a protein consisting of amino acids and sugar chains, which can bind to the target substance 130.

Although the bioreceptor 120 is not limited in type, it may be selected from a group consisting of a protein antibody, an aptamer, an enzyme, a nucleic acid, a DNA, an RNA, a cell, a biometic, protein, an organic compound and a polymer in a specific exemplary embodiment. An adequate bioreceptor may be selected depending on the type of the target substance. For example, when the target substance is cyt c, the bioreceptor may be a protein antibody.

The substrate may 110 be a nonmetallic material selected from a group consisting of silicon (Si), gallium arsenide (GaAs), glass, quartz and a polymer, although not being necessarily limited thereto. In a specific exemplary embodiment, the substrate may be glass.

Meanwhile, a blocking molecule 121 may be attached to the surface of the substrate 110 where the bioreceptor 120 is not attached. The blocking molecule 121 may be one or more selected from a group consisting of bovine serum albumin (BSA), casein and skim milk. As a specific exemplary embodiment, the blocking molecule 121 may be bovine serum albumin (BSA).

The metal nanoparticles 140 may be one or more selected from a group consisting of gold (Au), silver (Ag), platinum (Pt), tin (Sn), indium (In), gallium (Ga), thallium (Tl), lead (Pb), bismuth (Bi) and aluminum (Al), although not being necessarily limited thereto. In a specific exemplary embodiment, the metal nanoparticles 140 may be gold (Au) nanoparticles.

The metal nanoparticles 140 may have a diameter of 10-100 nm on average. The metal nanoparticles 140 may have a diameter of 20-95 nm, 40-90 nm, 60-95 nm or 80 nm on average. For example, when the diameter of the metal nanoparticles is smaller than 10 nm, it may be impossible to settle down the nanoparticles through centrifugation. And, when the diameter of the metal nanoparticles exceeds 100 nm, synthesis may be impossible.

A metal layer may be formed on the target substance by the metal nanoparticles 140, and the metal layer may have a thickness of 10-100 nm on average.

Whereas the distance between the target substance 130 and the metal nanoparticles 140 has been mostly maintained to tens of nanometers by an antibody in the prior art, in the present disclosure, the distance between the target substance 130 and the metal nanoparticles 140 is smaller than 1 nm because the target substance 130 is coated directly on the metal nanoparticles 140. As a result, the SERS signal can be enhanced and improved very superiorly.

The present disclosure also provides a method for detecting a target substance using the surface-enhanced Raman scattering (SERS)-based substrate for detecting a target substance.

The detection of the target substance may be performed by SERS spectroscopy. The target substance may be analyzed quantitatively by measuring the amplification of the Raman scattering intensity arising from the binding of the target substance to the substrate.

In SERS, the intrinsic SERS signal generated when incident light strikes the surface of the metal nanoparticles depending on the oscillatory state of molecules is enhanced. Recently, the characteristic SERS signals of different substances are frequently used to qualitatively detect biomaterials. According to the present disclosure, the target substance located on the surface-enhanced Raman scattering (SERS)-based substrate for detecting a target substance may be detected by measuring the intensity of Raman signals in the wavelength range of 500-2000 $cm^{-1}$ on average through surface-enhanced Raman scattering (SERS). More specifically, the SERS signals may be measured by irradiating a laser with a wavelength of 785 nm on average to the substrate.

The target substance may be a protein, a nucleic acid, a DNA, an RNA, an enzyme, an organic molecule, a virus, an extracellular vesicle, a microvesicle, an exosome, a cell, a fat, a metabolite or a pathogen. In a specific exemplary embodiment, the target substance may be a protein.

That is to say, according to the present disclosure, detection sensitivity may be improved by enhancing SERS signals by attaching metal nanoparticles to a target substance through centrifugation. The present disclosure may provide a method for improving SERS signals for detection of a target substance, which includes: (a) a step of forming a primary capture structure (bioreceptor-target substance) by reacting a bioreceptor-attached substrate which binds specifically to a target substance and the target substance; and (b) a step of forming a secondary capture structure having a sandwich structure of bioreceptor-target substance-metal nanoparticle by centrifuging the substrate with the primary capture structure formed in the presence of a solution containing metal nanoparticles.

In the present disclosure, the "improvement" of SERS signals includes the amplification of signals, and the amplified SERS signals may contribute to improved detection sensitivity of the target substance.

In addition, the present disclosure provides a method for detecting a target substance using the method for improving SERS signals.

MODE FOR INVENTION

Hereinafter, the present disclosure will be described in detail through examples and test examples.

However, the following examples and test examples are for illustrative purposes only and the scope of the present disclosure is not limited by the examples and test examples.

<Example> Preparation of Protein Sensor

Step 1: Attachment of Target Protein

For immobilization of a target protein for an antigen-antibody reaction on a substrate, the method introduced in "One-step antibody immobilization-based rapid and highly-sensitive sandwich ELISA procedure for potential in vitro diagnostics." (*Scientific Reports*, 2014, 4, 4407) was used for surface treatment of a glass substrate protein chip.

Figure 4:
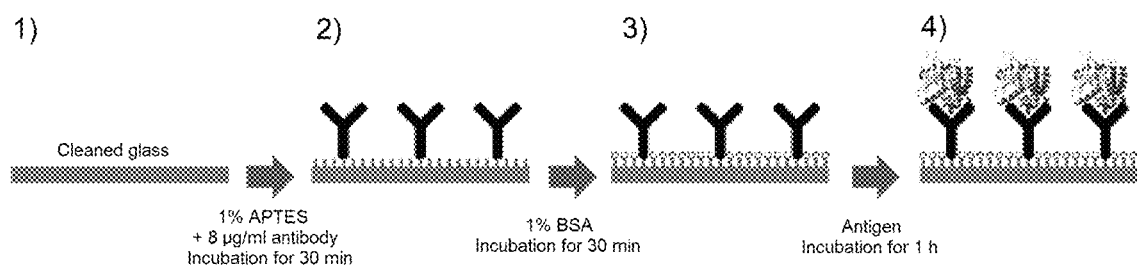
FIG. 4 schematically shows a process of attaching a target protein on a substrate.

The procedure of attaching a target protein to a substrate is described referring to FIG. 4.

First, a cover glass with a size of 5 cm×5 cm was dried after washing with water and alcohol. Then, after immersing the substrate in piranha solution ($H_2SO_4:H_2O_2$=7:3 (v/v)) for 30 minutes for hydroxylation of the surface and rinsing with water, the substrate was immersed for 30 minutes in an ethanol solution in which 1% 3-aminopropyltrimethoxysilane (APTMS) and a diluted solution of 8 μg/mL antibody were mixed for functionalization of the substrate surface with the organosilane amine group. Then, a bioreceptor was attached.

Thereafter, the substrate was immersed for 30 minutes in 1% bovine serum albumin (BSA) solution in order to block the APTES to which the antibody was not attached. Then, a target protein-attached substrate was prepared by inducing immunological binding by immersing the substrate in a solution containing the antigen cyt c.

Step 2: Attachment of Nanoparticles

Figure 5:
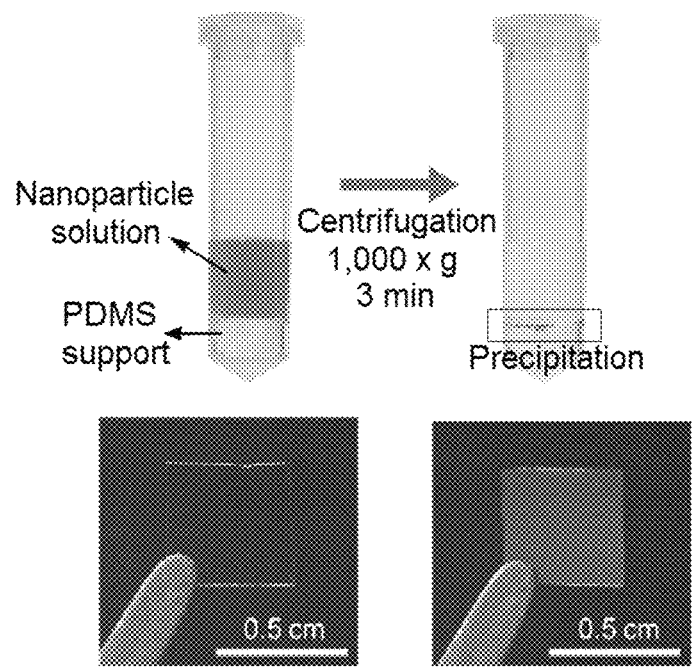
FIG. 5 shows a process of attaching nanoparticles based on centrifugation in an example of the present disclosure (Left part of FIG. 5: before centrifugation, Right part of FIG. 5: after centrifugation).

FIG. 5 shows a process of attaching nanoparticles based on centrifugation in an example of the present disclosure (left: before centrifugation, right: after centrifugation).

Referring to FIG. 5, in order to make the bottom surface of a centrifuge tube flat, a support made of a material such as PDMS, etc. was placed on the bottom surface of the tube and then the target protein antigen-bound substrate prepared in the step 1 was placed thereon.

Then, centrifugation was performed after filling 400 μL of a gold nanoparticle (BBI gold; average diameter=80 nm) colloid solution in the tube. The centrifugation was performed at 1,000×g for 3 minutes.

Thereafter, the prepared protein sensor was taken out from the tube, washed with distilled water, and then dried with nitrogen gas.

Figure 6A:
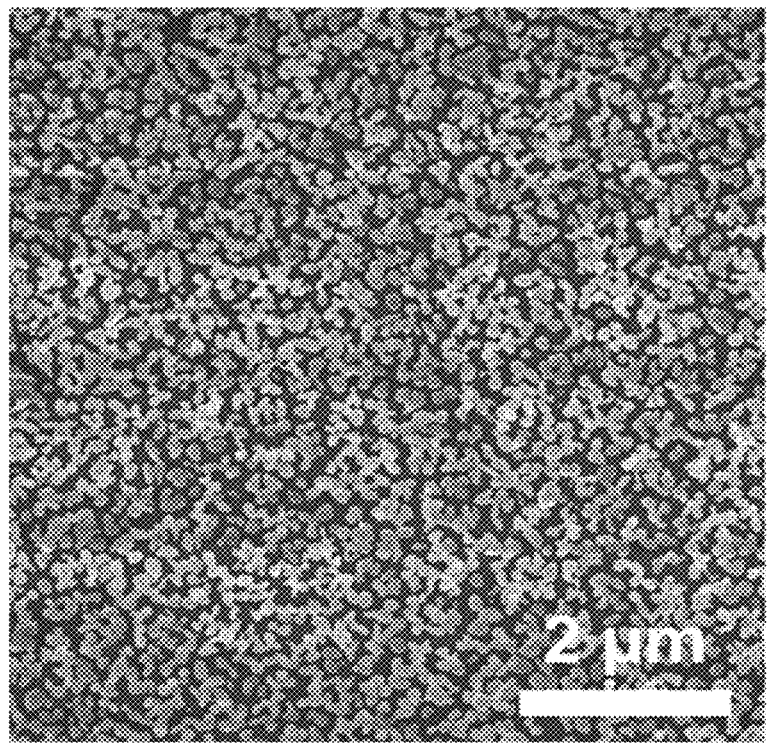
FIG. 6A shows a scanning electron microscopy (SEM) image of a substrate after centrifugation.
Figure 6B:
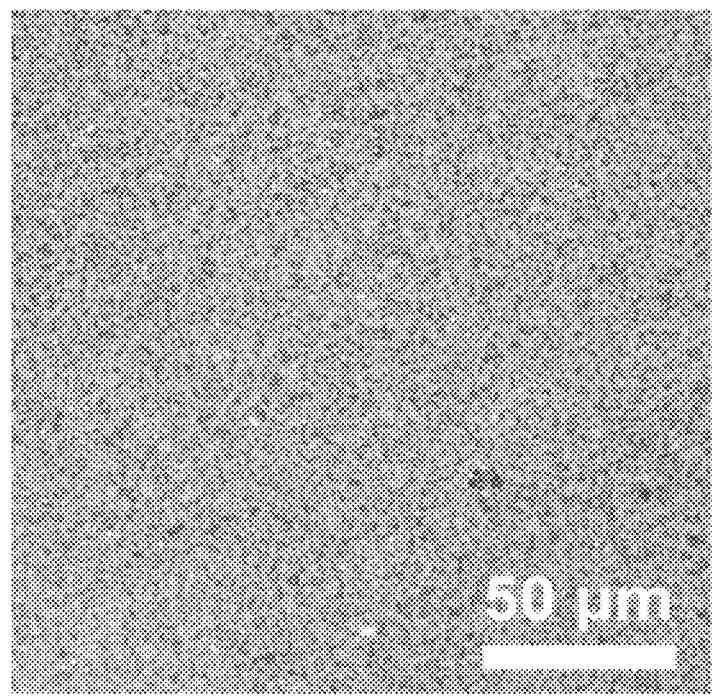
FIG. 6B shows a dark-field microscopy image of the substrate after centrifugation.

FIG. 6A shows the scanning electron microscopy (SEM) image of the substrate after centrifugation, and FIG. 6B shows the dark-field microscopy image of the substrate after centrifugation. As can be seen from FIGS. 6A and 6B, it was confirmed that gold nanoparticles were attached uniformly onto the substrate of the step 1.

Comparative Example

A protein sensor was prepared by immobilizing an antibody on gold nanoparticles and then attaching the antigen cyt c.

More specifically, after providing a gold nanoparticle solution on a glass substrate washed with piranha solution ($H_2SO_4:H_2O_2$=7:3 (v/v)) and drying the same, the substrate was treated for 12 hours with 10 mM mercaptopropionic acid (MPA) and then washed. Next, a substrate to which an antibody can be attached was prepared by treating the substrate for 1 hour with a 1:1 mixture solution of 0.2 M EDC and 0.2 M NHS and washing the same. Then, an antibody was introduced onto the substrate by treating the substrate with 0.1 mg/mL antibody for 1 hour and then washing the same.

Thereafter, a protein sensor was prepared by treating with 1% (w/v) BSA for 20 minutes for blocking and then attaching the antigen cyt c.

TEST EXAMPLES

Test Example 1. Signal Amplification Through Repeated Centrifugation

During the preparation of a protein sensor, the process of attaching nanoparticles to the target protein-attached substrate by centrifugation was repeated. The SEM images and observable color change of the substrate depending on the repeated centrifugation (cycle numbers) were investigated and the SERS signals of the target protein were measured.

Figure 7A:
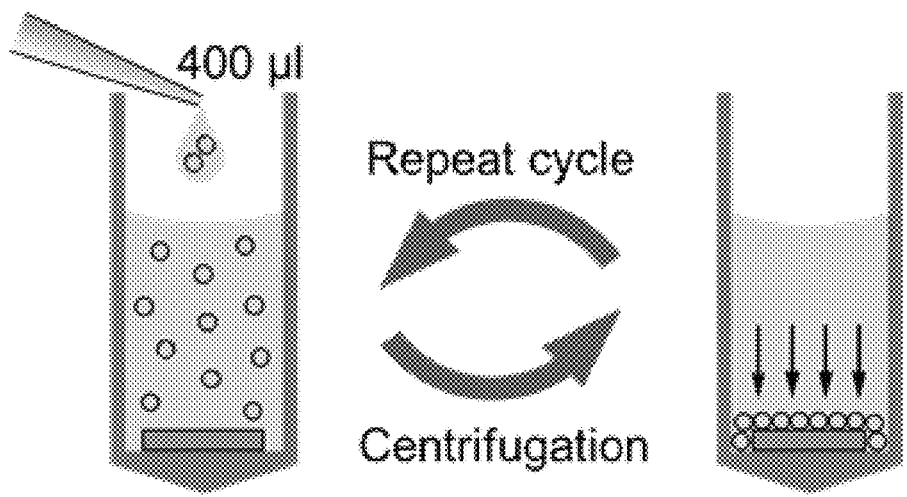
FIG. 7A schematically shows a centrifugation process.
Figure 7B:
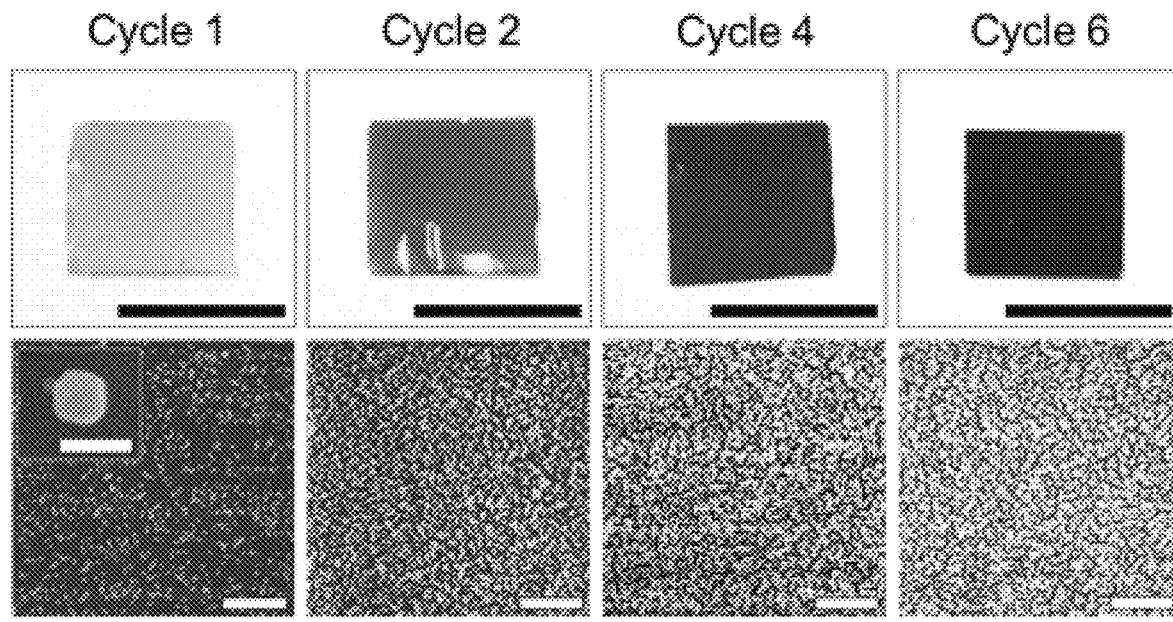
FIG. 7B shows the color change and SEM images of a substrate depending on repetition of centrifugation (number of cycles)
Figure 7C:
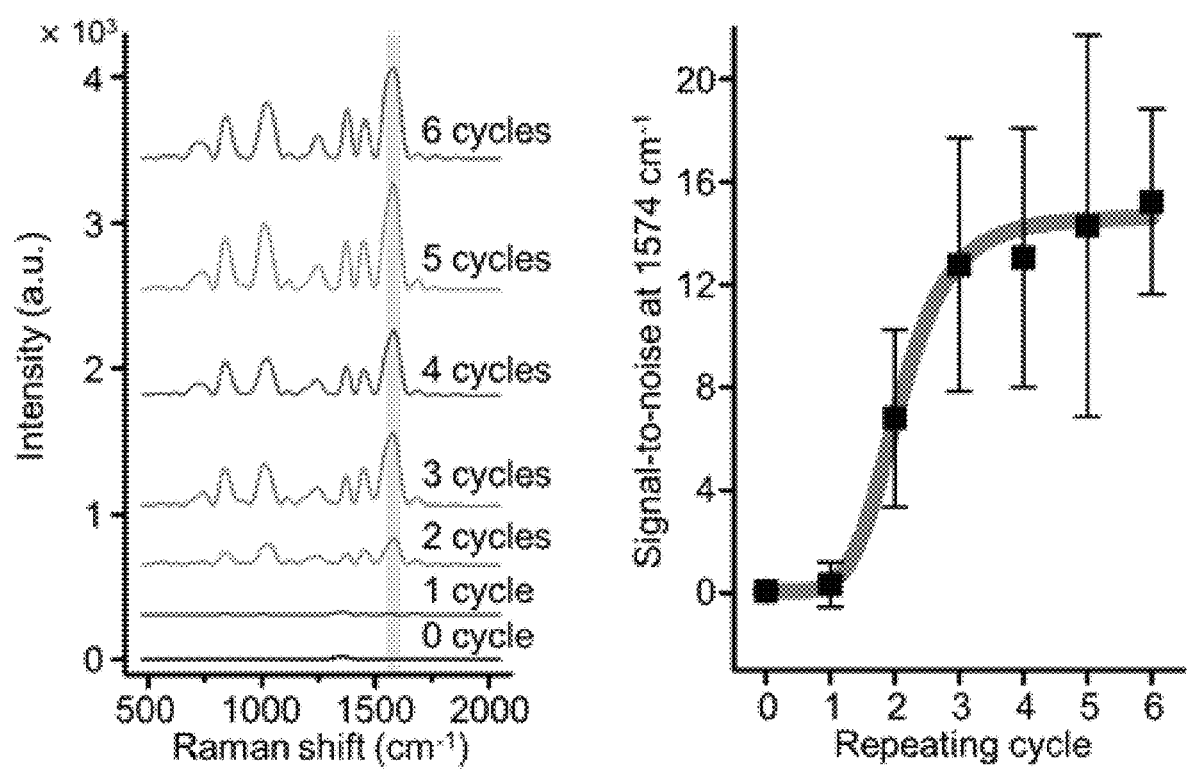
FIG. 7C shows the SERS signal of a target protein depending on repetition of centrifugation (number of cycles).

The result is shown in FIGS. 7A, 7B, and 7C.

FIG. 7A schematically shows the centrifugation process, FIG. 7B shows the color change and SEM images of the substrate depending on the repetition of centrifugation (number of cycles), and FIG. 7C shows the SERS signal of the target protein depending on the repetition of centrifugation (number of cycles).

Referring to FIGS. 7A and 7B, it was confirmed from the SEM images and observable color change that the number of the attached nanoparticles is increased gradually as the centrifugation process is repeated.

And, from FIG. 7C, it was confirmed that the intensity of the SERS signals of the target protein was also increased depending on the repeated centrifugation (cycle numbers). The increase in the signal intensity was slightly decreased after 3 times of repetition.

That is to say, it was confirmed that about 3 times of repetition is sufficient for signal amplification.

Test Example 2. Analysis of Uniformity of Nanoparticle Coating

Gold nanoparticles were coated on the surface of a SERS probe by introducing an amine group onto the surface through APTES and then treating with 4-aminothiophenol (4-ATP).

Then, spectrum analysis was conducted. More specifically, spectra were analyzed while moving detection spots with 2-μm intervals up to 120 μm or for randomly chosen detection spots. The result is shown in FIG. 8.

Figure 8A:
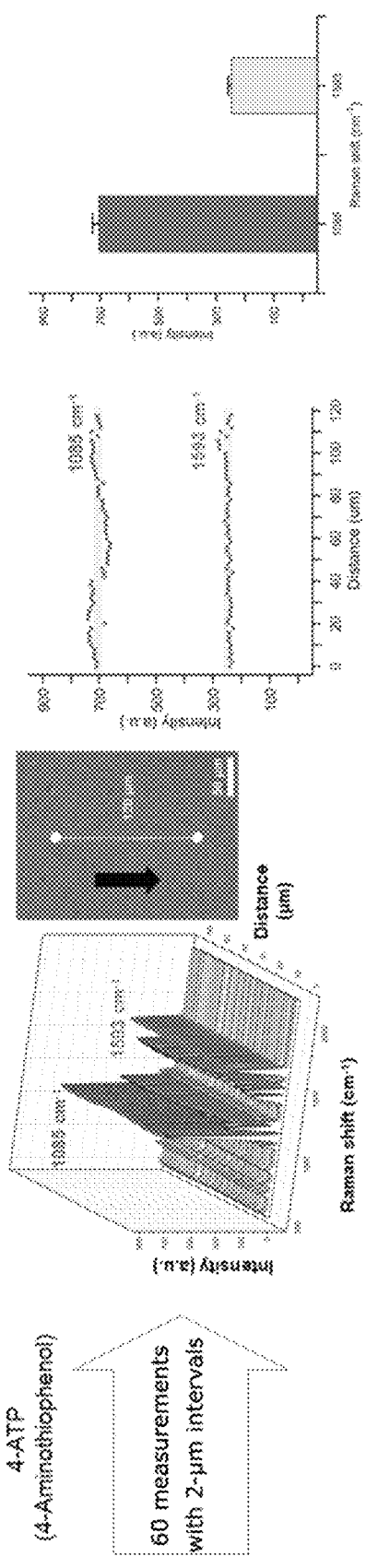
FIGS. 8A and 8B show results of analyzing spectra, more specifically.
Figure 8B:
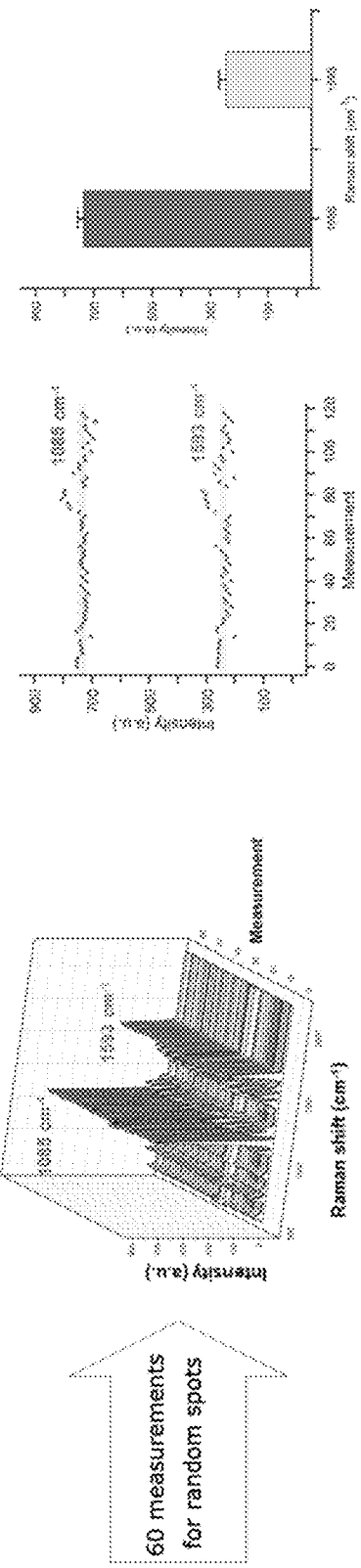

FIG. 8A shows the result of analyzing the spectra while moving detection spots with 2-μm intervals up to 120 μm, and FIG. 8B shows the result of analyzing the spectra for randomly chosen detection spots.

Referring to FIGS. 8A and 8B, the signal of 4-ATP was very uniform when the spectra were analyzed while moving detection spots with 2-μm intervals up to 120 μm.

In addition, the same result was obtained for the randomly chosen detection spots, which confirms that a uniform substrate can be manufactured by the method according to the present disclosure.

Test Example 3. Detection of Signals of Target Protein

The signals of C-reactive protein (target protein) were detected by surface-enhanced Raman scattering (SERS) using the protein sensors prepared in Example and Comparative Example.

Specifically, the surface-enhanced Raman scattering (SERS) spectra were detected using the Nicolet Raman spectrometer (Almeca XR) and the antigen signal detection efficiency was calculated based on the result.

Figure 9A:
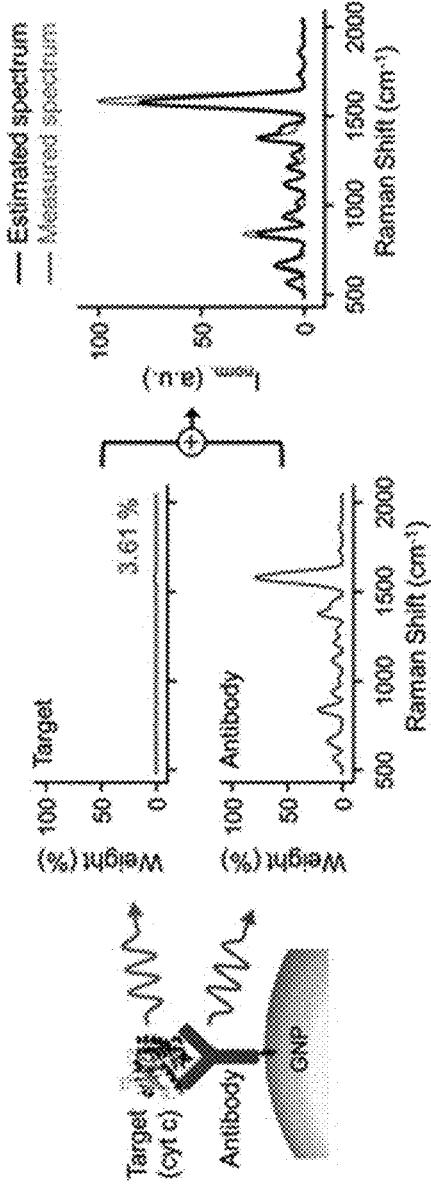
FIGS. 9A and 9B show results of detecting the signal of a target protein using protein sensors manufactured in Example and Comparative Example (9A: Example, 9B: Comparative Example).
Figure 9B:
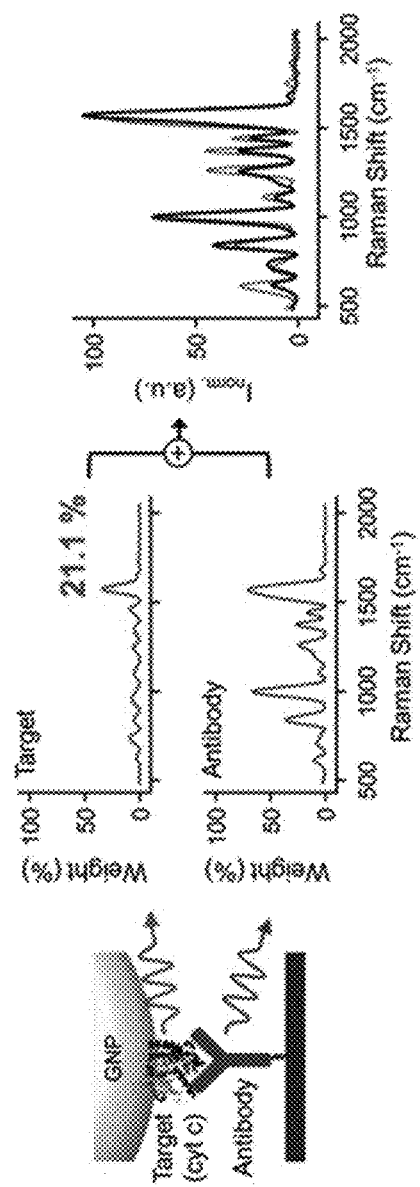

The result is shown in FIGS. 9A and 9B.

FIGS. 9A and 9B show the results of detecting the signals of the target protein using the protein sensors manufactured in Example and Comparative Example (9A: Example, 9B: Comparative Example).

The antigen signal detection efficiency was calculated according to [Equation 1].

$$S_{total} = W_{ab} \times S_{ab} + W_{cytc} \times S_{cytc}$$ [Equation 1]

wherein $S_{total}$ is the combined signal, $W_{ab}$ is the weight for the antibody signal, and $S_{ab}$ is the antibody signal, and $W_{cytc}$ is the weight for the antigen signal, and $S_{cytc}$ is the antigen signal.

The signal detected by the protein sensor will be a linear combination of the Raman signal of the antigen (cytochrome c) and the signal of the antibody. Therefore, after acquiring the SERS signal of the antibody in the state where only the antibody is attached, the signal most similar to the detected signal was found from linear combinations of the Raman signal of the antigen (cytochrome c) and the antibody signal.

As a result, the protein sensor manufactured in Example exhibited superior antigen signal detection efficiency as compared to the protein sensor manufactured in Comparative Example. Specifically, whereas the antigen signal detection efficiency was only about 3.61% for Comparative Example, the antigen signal detection efficiency was about 6 times higher for Example.

In conclusion, it is thought that the protein sensor of the present disclosure exhibits superior signal detection efficiency as compared to Comparative Example because the distance between the gold nanoparticles and the target antigen (target protein) is narrow since the single layer of gold nanoparticles is attached directly to the target protein.

DETAILED DESCRIPTION OF MAIN ELEMENTS

100: surface-enhanced Raman scattering (SERS)-based substrate for detecting target substance
110: substrate
120: bioreceptor
121: blocking molecule
130: target substance
140: metal nanoparticles

INDUSTRIAL APPLICABILITY

The present disclosure relates to a method for manufacturing a surface-enhanced Raman scattering (SERS)-based substrate for detecting a target substance, etc. Since the present disclosure can improve the detection sensitivity of a target substance, the present disclosure is expected to be widely applicable to molecular diagnostics, etc.

The invention claimed is:

1. A method for manufacturing a surface-enhanced Raman scattering (SERS)-based substrate for detecting a target substance, comprising:
    a step of forming a primary capture structure with a target substance and a bioreceptor bound by immersing a bioreceptor-attached substrate in a sample solution comprising a target substance;
    a step of disposing the substrate with the primary capture structure formed in a centrifuge tube and adding a solution comprising metal nanoparticles into the centrifuge tube; and
    a step of forming a secondary capture structure directly coating the metal nanoparticles on a surface of the target substance by operating the centrifuge tube.

2. The method for manufacturing a surface-enhanced Raman scattering (SERS)-based substrate for detecting a target substance according to claim 1, wherein the bioreceptor-attached substrate is one prepared by a step of attaching the bioreceptor to the substrate by immersing the substrate in a solution containing a surface modifier and a bioreceptor; and a step of attaching a blocking molecule onto a portion of a surface of the substrate without the bioreceptor attached.

3. The method for manufacturing a surface-enhanced Raman scattering (SERS)-based substrate for detecting a target substance according to claim 2, wherein the blocking molecule is one or more selected from a group consisting of bovine serum albumin (BSA), casein and skim milk.

4. The method for manufacturing a surface-enhanced Raman scattering (SERS)-based substrate for detecting a target substance according to claim 1, wherein the solution comprising the metal nanoparticles has a concentration of $1 \times 10^9$ to $1 \times 10^{12}$ particles/mL on average.

5. The method for manufacturing a surface-enhanced Raman scattering (SERS)-based substrate for detecting a target substance according to claim 1, wherein, in the step of forming the secondary capture structure, the centrifuge tube is centrifugated at 1,000-6,000×g for 2-5 minutes.

6. The method for manufacturing a surface-enhanced Raman scattering (SERS)-based substrate for detecting a target substance according to claim 5, wherein the step of forming the secondary capture structure is repeated 3 times or more.

7. The method for manufacturing a surface-enhanced Raman scattering (SERS)-based substrate for detecting a target substance according to claim 1, wherein, in the step of forming the secondary capture structure, the secondary capture structure is formed as the target substance is sandwiched between the bioreceptor and the metal nanoparticles.

8. The method for manufacturing a surface-enhanced Raman scattering (SERS)-based substrate for detecting a target substance according to claim 1, which further comprises, after the step of forming the secondary capture structure, a step of attaching a Raman dye on a surface of the metal nanoparticles.

9. The method for manufacturing a surface-enhanced Raman scattering (SERS)-based substrate for detecting a target substance according to claim 1, wherein the metal nanoparticles are one or more selected from a group consisting of gold (Au), silver (Ag), platinum (Pt), tin (Sn), indium (In), gallium (Ga), thallium (Tl), lead (Pb), bismuth (Bi) and aluminum (Al).

10. The method for manufacturing a surface-enhanced Raman scattering (SERS)-based substrate for detecting a target substance according to claim 1, wherein the metal nanoparticles have a diameter of 10-100 nm on average.

\* \* \* \* \*